United States Patent
Weihua (10) Patent No.: US 9,522,139 B2
(45) Date of Patent: Dec. 20, 2016

(54) FRUCTOSE 1, 6-BIPHOSPHATASES AS NEW TARGETS FOR DIAGNOSING AND TREATING BREAST CANCER BRAIN METASTASIS

(71) Applicant: The University of Houston System, Houston, TX (US)

(72) Inventor: Zhang Weihua, Houston, TX (US)

(73) Assignee: University of Houston System, Houston, TX (US)

( * ) Notice: Subject to any disclaimer, the term of this patent is extended or adjusted under 35 U.S.C. 154(b) by 429 days.

(21) Appl. No.: 13/676,308

(22) Filed: Nov. 14, 2012

(65) Prior Publication Data
US 2013/0143910 A1 Jun. 6, 2013

Related U.S. Application Data

(60) Provisional application No. 61/559,796, filed on Nov. 15, 2011.

(51) Int. Cl.
| | |
|---|---|
| *A61K 38/00* | (2006.01) |
| *A61K 31/404* | (2006.01) |
| *A61K 31/426* | (2006.01) |
| *A61K 31/4184* | (2006.01) |
| *A61K 31/437* | (2006.01) |
| *A61K 31/435* | (2006.01) |
| *A61K 31/343* | (2006.01) |

(52) U.S. Cl.
CPC ......... *A61K 31/437* (2013.01); *A61K 31/343* (2013.01); *A61K 31/404* (2013.01); *A61K 31/4184* (2013.01); *A61K 31/426* (2013.01); *A61K 31/435* (2013.01); *A61K 38/005* (2013.01)

(58) Field of Classification Search
CPC ............... A61K 31/404; A61K 31/426; A61K 31/4184; A61K 38/005
See application file for complete search history.

(56) References Cited

U.S. PATENT DOCUMENTS 4,291,048 A * 9/1981 Gold ............................ 514/419
6,489,476 B1 * 12/2002 Dang ........................... 544/232

OTHER PUBLICATIONS

Chen, et al., "Gain of Glucose-Independent Growth upon Metastasis of Breast Cancer Cells to the Brain," Molecular and Cellular Pathobiology, Cancer Research, 75(3), Feb. 1, 2015.
Wright, et al., "3-(2-Carboxy-ethyl)-4,6-dichloro-1H-indole-2-carboxylic Acid: An Allosteric Inhibitor of Fructose-1,6-bisphosphatase at the AMP Site," Bioorganic & Medicinal Chemistry Letters 13 (2003), Mar. 6, 2003.
Tominaga, Naoomi, et al., "Brain metastatic cancer cells release microRNA-181c-containing extracellular vesicles capable of destructing blood-brain barrier," Nature Communications, Apr. 1, 2015, pp. 1-12.
Burnett, Riesa M., et al. "Organ-specific adaptive signaling pathway activation in metastatic breast cancer cells," Oncotarget, vol. 6 No. 14, Mar. 2015, pp. 12682-12696.
Kosaka, Nobuyoshi, "Decoding the Secret of Cancer by Means of Extracellular Vesicles," Journal of Clinical Medicine 2016, 5, 22, Feb. 4, 2016, pp. 1-11.
Baron, B. M., et al., "Potent Indole- and Quinoline-Containing N-Methyl-D-Aspartate Antagonists Acting at the Strychnine-Insensitive Glycine Binding Site," The Journal of Pharmacology and Experimental Therepeutics, vol. 262 No. 3, May 18, 1992, pp. 947-956.
Millan, M.J., et al., "Chemically-diverse ligands at the glycine B site coupled to N-methyl-D-Aspartate (NMDA) receptors selectively block the late phase of formalin-induced pain in mice," Neuroscience Letters (1994), pp. 139-143.
Fidler, Isaish, et al., "The Biology of Brain Metastasis," The Cancer Journal, vol. 24 No. 4, Jul./Aug. 2015, pp. 284-293.

* cited by examiner

*Primary Examiner* — Samira Jean-Louis
(74) *Attorney, Agent, or Firm* — Blank Rome LLP (57) ABSTRACT

A method and composition for treating cancer cells that targets fructose-1,6-biphosphatase (EC:3.1.3.11) enzymes (FBPs, type 1 and type 2) and/or their respective pathways. In one embodiment, inhibitors of FBPs or FBPs pathways are administered to a patient to treat brain cancer metastasis. In another embodiment, the present invention is particularly well suited for treating cancer cells that generally survive under glucose-independent conditions, or any other condition where cancer cells produce glucose via FBPs mediated pathways.

9 Claims, 5 Drawing Sheets

FRUCTOSE 1, 6-BIPHOSPHATASES AS NEW TARGETS FOR DIAGNOSING AND TREATING BREAST CANCER BRAIN METASTASIS

CROSS-REFERENCES TO RELATED APPLICATIONS

This application claims priority to U.S. provisional application No. 61/559,796, filed on Nov. 15, 2011, and U.S. nonprovisional application Ser. No. 13/676,308, filed on Nov. 14, 2012, which are herein incorporated by reference in their entirety.

GOVERNMENTAL SPONSORSHIP

Not Applicable.

FIELD OF THE INVENTION

The present invention is directed to compositions and methods for diagnosing and treating cancer cells by targeting fructose-1,6-biphosphatase(EC:3.1.311) enzymes (FBPs, type 1 and type 2) and/or their respective pathways. More specifically, the present invention is particularly well suited for diagnosing and treating cancer cells that generally survive under glucose-independent conditions, such as but not limited to brain metastatic breast cancer cells, and by extension is applicable to any other condition where cancer cells produce glucose via FBPs mediated pathways Inhibitors of FBPs are well known and have been developed in laboratories with the goal of treatment of diseases such as diabetes. Our current finding reveals that inhibitors of FBPs could be used for prevention and treatment of cancer brain metastases.

BACKGROUND OF THE INVENTION

Cancer cells consume more nutrients and energy than non-malignant cells due to altered metabolisms (Koppenol, et al., Otto Warburg's contributions to current concepts of cancer metabolism, Nat Rev Cancer 11, 325-337 (2011)). Elevated aerobic glycolysis/fermentation, called the Warburg effect, is commonly used by cancer cells for sustaining growth and survival (Ferreira, L. M., Cancer metabolism: the Warburg effect today, Exp Mol. Pathol. 89, 372-380 (2010)). Amino acids, such as glutamine, can be abducted for energy production when glucose is not sufficiently available (DeBerardinis, et al., Beyond aerobic glycolysis: transformed cells can engage in glutamine metabolism that exceeds the requirement for protein and nucleotide synthesis, Proc. Nat'l Acad. Sci. USA 104, 19345-19350 (2007)). Enhanced oxidation of branched chain amino acids (BCAA), valine, leucine and isoleucine, occurs in cancers at late stage (Baracos, et al., Investigations of branched-chain amino acids and their metabolites in animal models of cancer, J. Nutr. 136, 237S-242S (2006); Beck, et al., Nitrogen excretion in cancer cachexia and its modification by a high fat diet in mice, Cancer Res. 49, 3800-3804 (1989); Pisters, et al., Protein and amino acid metabolism in cancer cachexia: investigative techniques and therapeutic interventions, Crit. Rev. Clin. Lab. Sci. 30, 223-272 (1993)). The driving force of altered metabolisms in cancer remains unclear. One possible cause is intrinsic, such as the malignant tumor cells' high demand for energy and building blocks, including amino acids for protein synthesis, nucleic acids for DNA and RNA syntheses, and fatty acids for membranous structures (Vander et al., Understanding the Warburg effect: the metabolic requirements of cell proliferation, Sci. 324, 1029-1033 (2009)). In support of this theory, it has recently been found that upregulation of an ATP hydrolase, ectonucleoside triphosphate diphosphohydrolase 5—which is induced by the PI3K pathway that promotes cell proliferation and survival—enhances cancer metabolism (Fang, M., et al., The ER UDPase ENTPD5 promotes protein N-glycosylation, the Warburg effect, and proliferation in the PTEN pathway, Cell 143, 711-724 (2010)).

Another possible cause is extrinsic, such as tissue environmental pressure, including hypoxia and ectopic microenvironment of the host organ of metastasis to which metastatic cancer cells have to adapt for survival and growth (Fidler, I. J., The organ microenvironment and cancer metastasis, Differentiation 70, 498-505 (2002); Langley, R. R. & Fidler, I. J. The seed and soil hypothesis revisited—the role of tumor-stroma interactions in metastasis to different organs. Int J Cancer 128, 2527-2535 (2011); Martinez-Outschoorn, U. E., et al., Stromal-epithelial metabolic coupling in cancer: Integrating autophagy and metabolism in the tumor microenvironment, Int. J. Biochem. Cell Biol. 43, 1045-1051 (2011)). The microenvironment of different tissues differs significantly. Metastatic tumor cells can reach many organs, but grow in only specific organs (Fidler, I. J., The organ microenvironment and cancer metastasis, Differentiation 70, 498-505 (2002)). The compatibility between tumor cells and the microenvironment of host tissue determines the outcome of metastasis. For example, studies have shown that cancer associated stromal cells are reprogrammed in favor of metabolizing lactate extruded by cancer cells (Martinez-Outschoorn, U. E., et al., Stromal-epithelial metabolic coupling in cancer: Integrating autophagy and metabolism in the tumor microenvironment, Int. J. Biochem. Cell Biol. 43, 1045-1051 (2011)).

Breast cancer is one of the most common tumors that present with brain metastasis, a late complication of progressive metastatic disease for which effective treatment options are limited. The microenvironment of the brain plays a key role in the development of the therapeutic resistance of brain metastasis (Steeg, P. S., Camphausen, K. A. & Smith, Q. R. Brain metastases as preventive and therapeutic targets. Nat Rev Cancer 11, 352-363 (2011)). The interstitial space of the brain is characterized by low levels of glucose (Fellows, L. K., et al., Extracellular brain glucose levels reflect local neuronal activity: a microdialysis study in awake, freely moving rats, J. Neurochem. 59, 2141-2147 (1992); Hu, Y. et al., Rapid changes in local extracellular rat brain glucose observed with an in vivo glucose sensor, J. Neurochem. 68, 1745-1752 (1997)), high levels of glutamine (Yudkoff, M., et al., Brain glutamate metabolism: neuronal-astroglial relationships, Dev. Neurosci. 15, 343-350 (1993)), and an intermediate metabolite of BCAAs, the branched chain alpha-ketoacids (BCKA) (Yudkoff, M., Brain metabolism of branched-chain amino acids, Glia 21, 92-98 (1997)). Glutamine and BCAAs can serve as energy substrates (Daikhin, Y. et al., Compartmentation of brain glutamate metabolism in neurons and glia, J. Nutr. 130, 1026S-1031S (2000)). The rich contents of glutamine and BCAAs in the interstitial microenvironment may contribute to the survival of cancer cells growing in the brain. Expressions of mRNA of glycolytic enzymes were found to be increased in the brain metastatic breast cancer cells (Harris, R. A. et al., Overview of the molecular and biochemical basis of branched-chain amino acid catabolism, J. Nutr. 135, 1527S-1530S (2005)); however, the role of carbon sources other than glucose for the survival/growth of brain metastatic breast cancer cells remains to be investigated. Because brain metastatic breast cancer cells (and some other cancer cells) are able to thrive in glucose-free medium, those cells are resistant to contemporary cancer therapies that target glucose pathways. Therefore, there is a need in the art for methods of treating cancer cells that survive in glucose-independent conditions.

SUMMARY OF THE INVENTION

In one embodiment of the present invention, a method is disclosed for treating cancer by administering to a patient inhibitors of FBPs or FBPs pathways. This method is based on the finding that brain metastatic breast cancer cells survive and grow independently of the presence of glucose, which is attributed to enhanced activities of branched chain amino acids oxidation and gained ability of gluconeogenesis. As a result, targeting amino acid oxidation or the gluconeogenesis pathway offers a new avenue for the diagnostic and treatment of breast cancer brain metastasis, and by extension to any other cancer cells that possess active fructose-1,6-biphosphatase (EC:3.1.3.11) enzymes.

In another embodiment of the present invention, cancer cells are treated with compositions comprising inhibitors of FBPs or FBPs pathways.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the present disclosure. It should be understood, however, that the invention is not limited to the precise arrangements and instrumentalities shown FIG. 1. Shows various characterizations of MDA-MB-231Br3 cells.

DETAILED DESCRIPTION OF THE INVENTION

The following references are incorporated by reference in their entirety: Koppenol, et al., Otto Warburg's contributions to current concepts of cancer metabolism, Nat. Rev. Cancer 11, 325-337; Ferreira, L. M., Cancer metabolism: the Warburg effect today, Exp. Mol. Pathol. 89, 372-380 (2010); DeBerardinis, R. J., et al., Beyond aerobic glycolysis: transformed cells can engage in glutamine metabolism that exceeds the requirement for protein and nucleotide synthesis, Proc. Natl. Acad. Sci. USA 104, 19345-19350 (2007); Baracos, et al., Investigations of branched-chain amino acids and their metabolites in animal models of cancer, J. Nutr. 136, 237S-242S (2006); Beck, et al., Nitrogen excretion in cancer cachexia and its modification by a high fat diet in mice, Cancer Res. 49, 3800-3804 (1989); Pisters, P. W. et al., Protein and amino acid metabolism in cancer cachexia: investigative techniques and therapeutic interventions, Crit. Rev. Clin. Lab Sci. 30, 223-272 (1993); Vander Heiden, M. G., et al., Understanding the Warburg effect: the metabolic requirements of cell proliferation, Science 324, 1029-1033 (2009); Fang, M., et al., The ER UDPase ENTPD5 promotes protein N-glycosylation, the Warburg effect, and proliferation in the PTEN pathway, Cell 143, 711-724 (2010); Fidler, I. J., The organ microenvironment and cancer metastasis, Differentiation 70, 498-505 (2002); Martinez-Outschoorn, U. E., et al., Stromal-epithelial metabolic coupling in cancer: Integrating autophagy and metabolism in the tumor microenvironment, Int. J. Biochem. Cell Biol. 43, 1045-1051 (2011); Fellows, L. K., et al., Extracellular brain glucose levels reflect local neuronal activity: a microdialysis study in awake, freely moving rats, J. Neurochem. 59, 2141-2147 (1992); Hu, Y., et al., Rapid changes in local extracellular rat brain glucose observed with an in vivo glucose sensor, J. Neurochem. 68, 1745-1752 (1997); Yudkoff, M., et al., Brain glutamate metabolism: neuronal-astroglial relationships, Dev. Neurosci. 15, 343-350 (1993); Yudkoff, M., Brain metabolism of branched-chain amino acids, Glia 21, 92-98 (1997); Daikhin, Y., et al., Compartmentation of brain glutamate metabolism in neurons and glia, J. Nutr. 130, 1026S-1031S (2000); Harris, R. A., et al., Overview of the molecular and biochemical basis of branched-chain amino acid catabolism, J. Nutr. 135, 1527S-1530S (2005); Chen, E. I., et al., Adaptation of energy metabolism in breast cancer brain metastases, Cancer Res. 67, 1472-1486 (2007); Yano, S., et al., Expression of vascular endothelial growth factor is necessary but not sufficient for production and growth of brain metastasis, Cancer. Res. 60, 4959-4967 (2000); Kovacevic, Z., et al., Mitochondrial metabolism of glutamine and glutamate and its physiological significance, Physiol. Rev. 63, 547-605 (1983); Li, C., et al., Green tea polyphenols modulate insulin secretion by inhibiting glutamate dehydrogenase, J. Biol. Chem. 281, 10214-10221 (2006); Chaffer, C. L., et al., A perspective on cancer cell metastasis, Science 331, 1559-1564 (2011); Langley, R. R., et al., The seed and soil hypothesis revisited—the role of tumor-stroma interactions in metastasis to different organs, Int. J. Cancer 128, 2527-2535 (2011); Steeg, P. S., et al., Brain metastases as preventive and therapeutic targets, Nat. Rev. Cancer 11, 352-363 (2011); Pellerin, L., Brain energetics (thought needs food), Curr. Opin. Clin. Nutr. Metab. Care 11, 701-705 (2008); del Amo, E. M., et al., M. Pharmacokinetic role of L-type amino acid transporters LAT1 and LAT2, Eur. J. Pharm. Sci. 35, 161-174 (2008); Ishiwata, K., et al., Re-evaluation of amino acid PET studies: can the protein synthesis rates in brain and tumor tissues be measured in vivo?, J. Nucl. Med. 34, 1936-1943 (1993); Ishiwata, K., et al., Brain tumor accumulation and plasma pharmacokinetic parameters of 2'-deoxy-5-18F-fluorouridine, Ann. Nucl. Med. 7, 199-205 (1993); Kirikae, M., et al., Quantitative measurements of regional glucose utilization and rate of valine incorporation into proteins by double-tracer autoradiography in the rat brain tumor model, J. Cereb. Blood Flow Metab. 9, 87-95 (1989); Previs, S. F., et al., Is there glucose production outside of the liver and kidney?, Annu Rev. Nutr. 29, 43-57 (2009); Kitas, E., et al., Sulfonylureido thiazoles as fructose-1,6-bisphosphatase inhibitors for the treatment of Type-2 diabetes, Bioorganic & Medicinal Chemistry Letters 20, 594-599 (2010); U.S. Pat. Nos. 7,371,739; 7,312,219; 7,285,543; 6,967,193; 6,919,322; 6,489,476; 6,399,782; 6,399,782; 6,294,672; 6,110,903; 6,107,274; 6,054,587.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. It should be understood that any one of the features of the invention may be used separately or in combination with other features. Other systems, methods, features, and advantages of the invention will be or become apparent to one with skill in the art upon examination of the drawings and the detailed description. It is intended that all such additional systems, methods, features, and advantages be included within this description, be within the scope of the present invention, and be protected by the accompanying claims.

Embodiments of the present invention relates to compositions and methods for diagnosing and treating cancer cells by targeting fructose-1,6-biphosphatase (EC:3.1.3.11) type enzymes and/or their respective pathways. More specifically, the present invention is particularly well suited for diagnosing and treating cancer cells that generally survive in a glucose-free medium, such as but not limited to brain metastatic breast cancer cells, and by extension is applicable to any other condition where cancer cells produce glucose via FBPs pathways. As a consequence, the development of appropriate inhibitors to this enzyme and its related pathways offers a new avenue for the treatment of diseases where cancer cells produce glucose via FBPs pathways. This invention takes advantage of the elucidation herein that FBPs and their related pathways are responsible for cancer cell survival in glucose-independent conditions. It also takes advantage of the fact that inhibitors of FBPs are well known and have been developed in laboratories with the goal of treatment of diseases such as diabetes.

The present invention teaches the importance of FBPs and their related pathways for the survival of breast cancer brain metastasis, as demonstrated by their ability to produce glucose and other metabolites in a glucose-free medium (which is met in the brain). The present invention is therefore useful in clinical applications. Gluconeogenic activity is not normally present in cells that are not originated from liver, kidney or intestine (Ishiwata, K., et al., Brain tumor accumulation and plasma pharmacokinetic parameters of 2'-deoxy-5-18F-fluorouridine, Ann. Nucl Med 7, 199-205 (1993)). Gaining the capacity of producing ribose from amino acids using part of the gluconeogenic pathway by upregulation of FBPs and increase oxidation of amino acids, provides the brain metastatic cells with external glucose independent survival and proliferation skills, production of ATP from amino acids oxidation and generation of building blocks for proliferation using the gluconeogenic pathway, both of which may serve as therapeutic targets for treatment of breast cancer brain metastasis.

Figure 1:
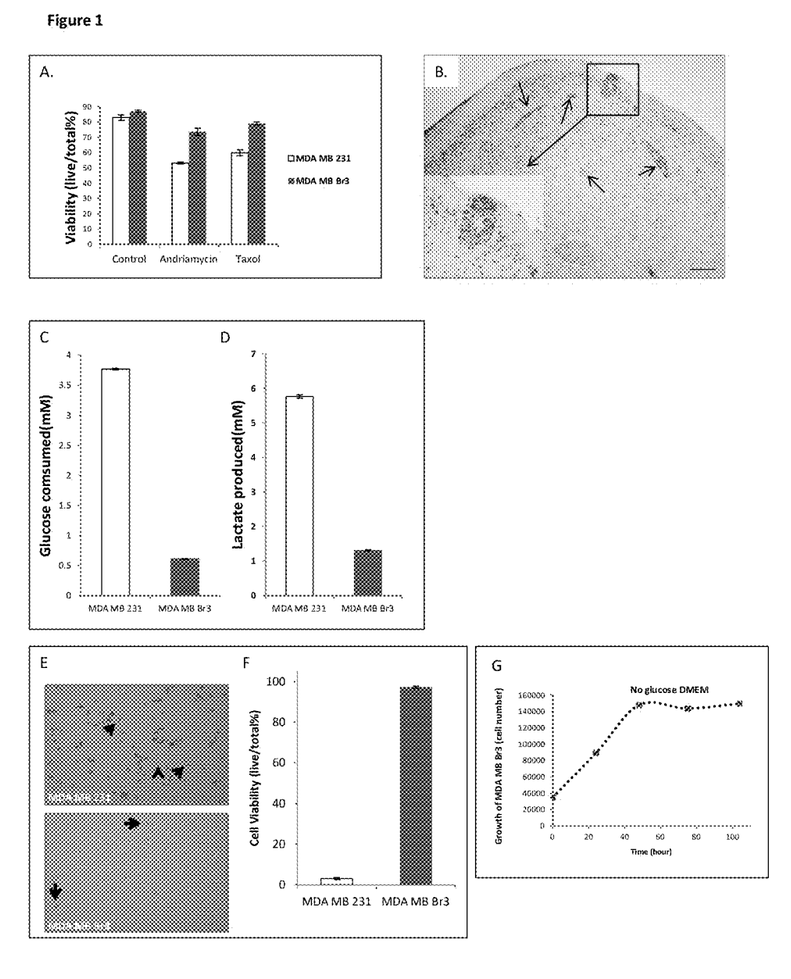

In some embodiments of the present invention brain metastatic breast cancer cells develop significant metabolic alterations to be able to survive in a glucose-free medium. By way of non-limiting example, cells from a metastatic breast cancer cell line, MDA-MB-231Br3, can be derived from MDA-MB-231 cells by three rounds of cloning from brain metastasis (e.g., by orthotopically implanting MDA-MB-231 cells in the brain of nude mice). The derived cells survive in glucose-free medium, which represents a shift from glucose dependency (in parental cells) to glucose independency (in MDA-MB-231Br3 cells). To test the ability of the derived cells to form spontaneous brain metastasis, these cells (5000 cells per injection) can be implanted into the mammary gland fat pad of female nude mice. Three months after tumor implantation, the brains of these mice can be harvested for metastasis analysis by sectioning. The MDA-MB-231Br3 cells show more resistance to chemotherapeutic reagents, such as adriamycin and Taxol®, than their parental cells, as shown in FIG. 1A (triplicates of samples are used in each group). As shown in FIG. 1B, spontaneous micro-brain metastases can be identified in at least 3 of 5 brains of tumor bearing mice. FIGS. 1C and 1D reveal that MDA-MB-231Br3 cells are significantly less glycolytic than their parental cells, as measured by the lower consumption of glucose and the lower production of lactate when such cells are cultured in MEM containing 5 mM glucose for 24 hours. By contrast, and as shown in FIGS. 1E, 1F and 1G, more than 95% of parental MDA-MB-231 cells die within 72 hours after glucose is removed from the cell culture medium, while brain metastatic MDA-MB-231Br3 cells remain completely viable. This embodiment demonstrates that metastatic MDA-MB-231Br3 cells are able to survive in a glucose-free medium by developing significant metabolic alterations, which represents a shift from glucose dependency (in parental cells) to glucose independency (in MDA-MB-231Br3 cells).

Figure 2:
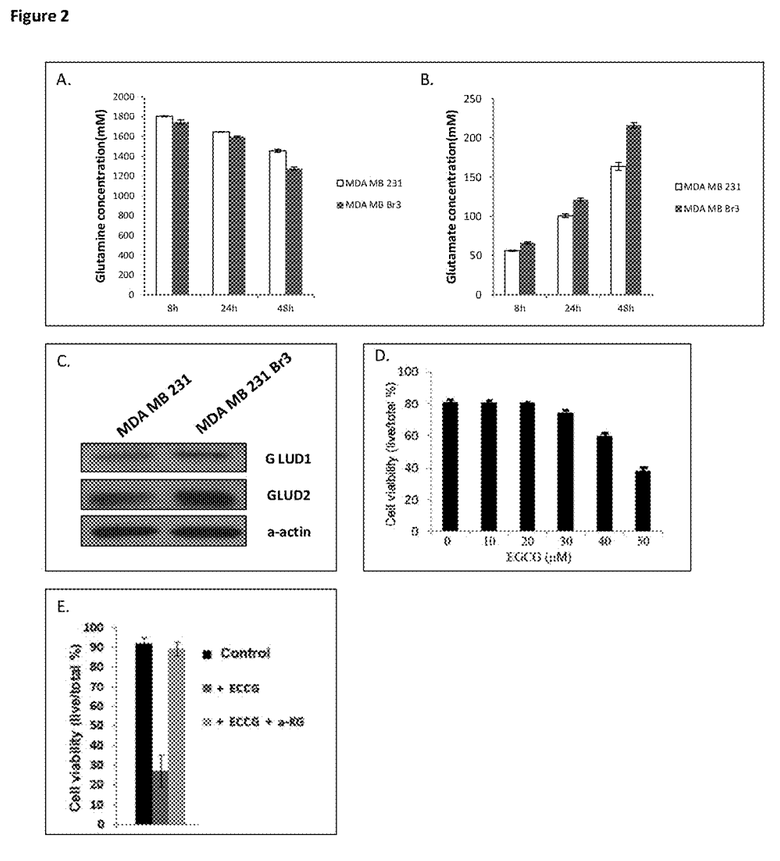
FIG. 2. Shows the role of glutamine metabolism in the survival of MDA-MB-231Br3 cells.

In other embodiments of the present invention brain metastatic breast cancer cells survive in glucose-free medium because of an active tricarboxylic acid cycle sustained by α-KG derived from glutamine/glutamate oxidation. This embodiment suggests that carbon sources other than (or in addition to) glucose may also be utilized by such cells to sustain survival. It is well established in the literature that beside glucose, amino acids can serve as energetic substrates. Considering the high levels of glutamine and BCAAs in the interstitial space of the brain, metabolisms of these two classes of amino acids probably play an important pro-survival role in brain metastatic cells. In fact, prior art teaches that glutamine can be metabolized to glutamate by glutaminase, and glutamate can be further oxidized by glutamate dehydrogenases (GLUD1 and 2 GLUD) (Kovacevic, Z. et al., Mitochondrial metabolism of glutamine and glutamate and its physiological significance. *Physiol. Rev.* 63, 547-605 (1983)) to a citric acid cycle intermediate metabolite α-ketoglutarate (α-KG). Therefore, in one embodiment, to determine the importance of glutamine in the survival of brain metastatic MDA-MB-231Br3 cells, the levels of glutamine and glutamate can be measured in parental MDA-MB-231 cells and brain metastatic MDA-MB-231Br3 cells when cultured in glucose-free medium for 24 hours. By way of non-limiting example, FIGS. 2A and 2B show that in the absence of glucose, MDA-MB-231Br3 cells consume more glutamine and produce more glutamate than their parental cells, indicating that brain metastatic cells possess an enhanced glutamine metabolism. This data is recorded from cells cultured in glucose-free medium for 8, 24 and 48 hours, with triplicates of samples used at each time point. To test whether these two types of cells exhibit differences in their ability to oxidize glutamate to α-KG, the expression levels of GLUD1 and GLUD2, as measured by Western blot, can be recorded. For example, FIG. 2C shows that MDA-MB-231 Br3 cells express a relatively higher amount of GLUD1 and GLUD2 relative to MDA-MB-231 cells. Glutamate is known to be one of the major sources for the production of α-ketoglutarate, a key metabolite that sustains the tricarboxylic acid (TCA) cycle. To test the role of glutamate derived α-KG in the survival of brain metastatic cancer cells, such cells can be treated with a GLUD inhibitor, namely epigallocatechin gallate (EGCG) (Li, C., et al. Green tea polyphenols modulate insulin secretion by inhibiting glutamate dehydrogenase. *J. Biol. Chem.* 281, 10214-10221 (2006)). As show in FIG. 2D, brain metastatic cells are more sensitive to GLUD inhibition in the absence of glucose than parental cells Inhibition of GLUD by EGCG causes a dose dependent cell death of MDA-MB-231Br3 cells cultured in glucose-free medium; that trend is reverted upon addition of α-KG. Furthermore, as shown in FIG. 2E, supplementation of α-KG completely rescues brain metastatic cells. This data indicates that an active TCA cycle sustained by α-KG derived from glutamine/glutamate is required for the survival of brain metastatic cells. For these tests, trypanblue uptake can used to identify dead cells, and triplicates of samples can be used in each group.

Figure 3:
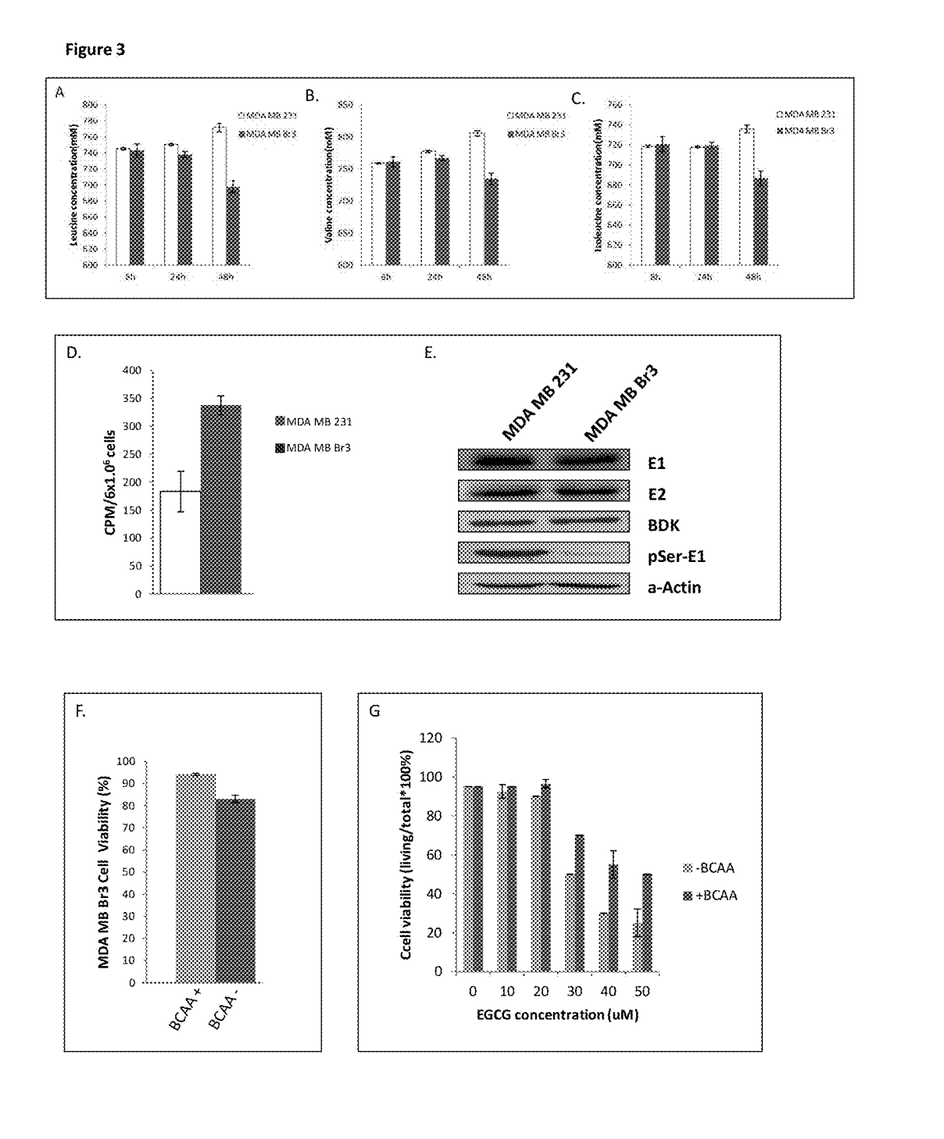
FIG. 3. Shows the role of BCAA metabolism in the survival of MDA-MB-231Br3 cells.

In yet another embodiment of the present invention, brain metastatic breast cancer cells possess an enhanced metabolism allowing them to consume valine, leucine, and isoleucine (BCAAs) for the purpose of securing their survival in a glucose-free medium. BCAAs are known to exist at high levels in the brain. By way of non-limiting example, to test the role of BCAAs in the survival of brain metastatic breast cancer cells, changes in the concentrations of BCAAs over time can be measured in MDA-MB-231 and MDA-MB-231Br3 cells when cultured in a glucose-free medium. As demonstrated in FIGS. 3A-C, the levels of BCAAs increase in the medium of the parental MDA-MB-231 cells and decrease in the medium of the MDA-MB-231Br3 cells, suggesting that brain metastatic cells only, and not parental cells, consume BCAAs (triplicates of samples used at each time point). To measure the ability of these two types of cells to oxidize BCAAs, $^{14}$C-Leucine can be added to the culture media and the resulting $^{14}CO_2$ measured after 8 hours of incubation. FIG. 3D shows that brain metastatic cells present a significant activity of BCAA oxidation. MDA-MB-231Br3 cells produce a significantly higher level of $^{14}CO_2$ from $^{14}$C-leucine than MDA-MB-231 cells (CPM, count per minute). To investigate the mechanism by which brain metastatic cells gain such higher activity of BCAA oxidation, the levels of the rate limiting enzymes of BCAA oxidation, branched chain ketoacids dehydrogenase E1 subunit (BCKDH-E1), the inactivated form of BCKDH-E1, pSer293-BCDKH-E1 (phosphorylated at serine 293 of the E1 subunit), the BCKDH inactivating kinase, and the branched chain ketoacids dehydrogenase kinase (BDK) can be determined in both brain metastatic cells and parental cells. For example, FIG. 3E shows a Western blot analysis of BCKDH-E1 (E1), BCKDH-E2, BDK, pSer293-BCKDH-E1 (pE1) in MDA-MB-231, and MDA-MB-231Br3 cells, where Actin is used as loading controls. While the total amounts of BCKDH-E1 and BDK are similar in both cell types, brain metastatic cells, however, exhibit a significantly lower level of pSer293-BCKDH-E1. This shows that brain metastatic cells have a higher ability to oxidize BCAAs. Also, to test the pro-survival role of BCAAs in MDA-MB-231Br3 cells, BCAAs can be removed from the glucose-free medium containing glutamine. For example, FIG. 3F shows that after 24 hours of culture, MDA-MB-231Br3 cells present a 10% decrease in cell survival, and, as shown in FIG. 3G, incremental removal of BCAAs from the glucose-free medium significantly sensitizes cells to GLUD inhibition by EGCG (for a 24 hour treatment). Together with results shown in FIG. 2, this data demonstrates that both glutamine/glutamate derived α-KG sustained TCA cycle and the oxidation of BCAAs are required for sufficiently maintaining the survival of brain metastatic cells. For these tests, trypanblue uptake can used to identify dead cells, and triplicates of samples can be used in each group.

In other embodiments of the present invention, brain metastatic breast cancer cells cultured in a glucose-free medium gain gluconeogenic capacity by up-regulating fructose-1,6-biphosphatase (EC:3.1.3.11) type 2 (FBP2). Prior art teaches that the gluconeogenic pathway is active in brain metastatic breast cancer cells. Since brain metastatic cells are able to grow and survive in the absence of glucose, the question that remains is how these cells manage to produce the basic building blocks, such as ribose, necessary for nucleotide synthesis, which further cancer cell proliferation. In the embodiment, MDA-MB-231Br3 cells usurp part of the gluconeogenic pathway to produce substrates for the formation of ribose-phosphate using amino acids such as glutamine. To test this fact, MDA-MB-231 cells and MDA-MB-231Br3 cells can be cultured for 6 hours in a glucose-free medium containing $^{13}$C-glutamine, which is followed by metabolite extraction. The levels of $^{13}$C-ribose-phosphate can be determined by LC-MS.

TABLE 1

$^{13}$C-glutamine produced$^{13}$C-phosphoribose can
be detected in MDA MB Br3 but not MDA MB 231P

| Sample | Ribose-phosphate | Ribose-phosphate_$^{13}$C |
|---|---|---|
| MDA MB 231P__1 | 233562.5 | ND |
| MDA MB 231P__2 | 191925.8 | ND |
| MDA MB Br3__1 | 264686.6 | 44943.82 |
| MDA MB Br3__2 | 297628.1 | 65265.43 |

Table 1 $^{13}$C-glutamine produced $^{13}$C-phosphoribose can be detected in MDA MB Br3 cells but not in MDA MB 231.

Figure 4:
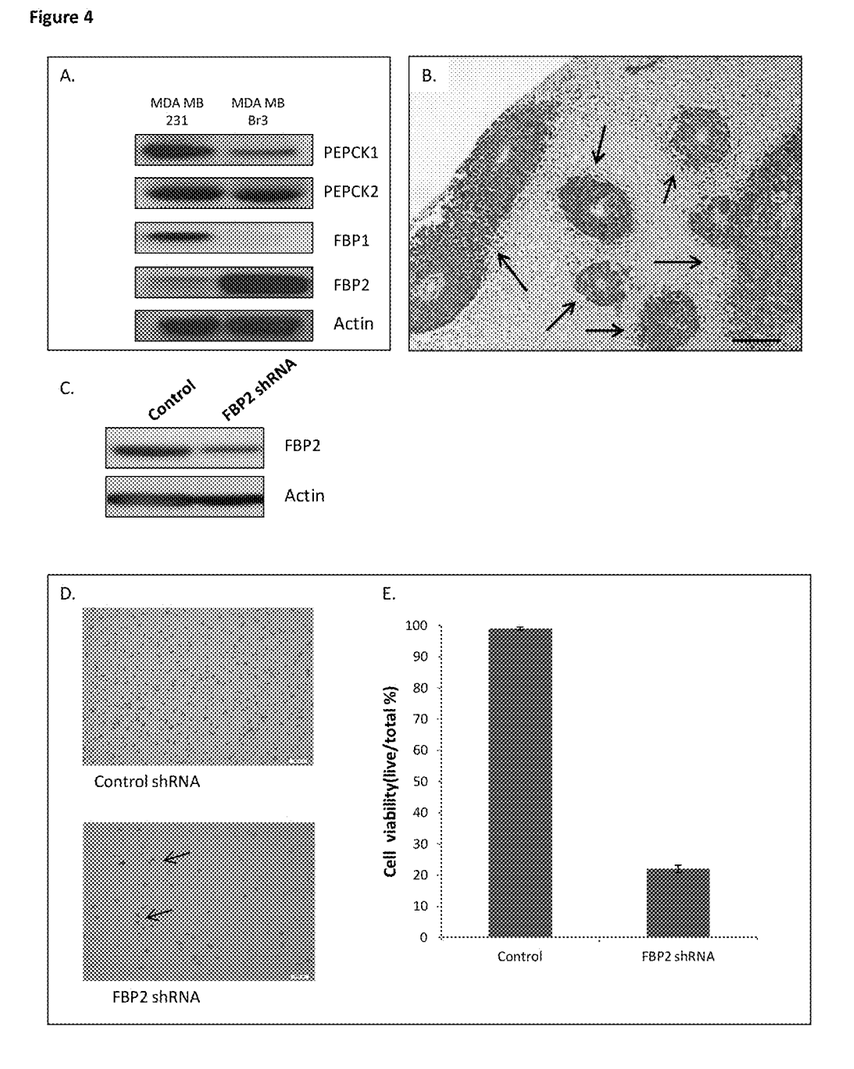
FIG. 4. Shows the role of glucogenic enzymes in the survival of breast cancer brain metastatic cells.

Table 1 above shows that brain metastatic MDA-MB-231Br3 cells only, and not parental MDA-MB-231 cells, produce ribose-phosphate from glutamine. These results demonstrate that at least part of the gluconeogenic pathway is active in brain metastatic cancer cells. Previous studies reveal there are two energy consuming rate limiting enzymes within the gluconeogenesis pathway. The first is phosphoenylpyruvate carboxykinases (PEPCK1 in the cytoplasm and PEPCK2 in the mitochondria) converting oxaloacetate to phosphoenylpyruvate (PEP). The second is fructose-1,6-bisphosphatases (EC:3.1.3.11) (FBP1 and FBP2) converting fructose-1,6-biphosphate to fructose-6-phosphate, which can be further converted into glucose-6-phosphate, a substrate of the pentose phosphate pathway, in order to produce ribose-phosphate needed for the production of nucleotides. Expression levels of these gluconeogenic rate limiting enzymes can be compared in both parental and brain metastatic cancer cells. By way of non-limiting example, FIG. 4A, which is a Western blot analyses of PEPCK1, PEPCK2, FBP1, FBP2 in MDA-MB-231 and MDA-MB-231Br3 cells (actin used as loading controls), shows that in brain metastatic cells, PECK2 remains unchanged, while FBP1 and PEPCK1 are significantly down-regulated; however, FBP2 is significantly up-regulated. Thus, mitochondrial PEPCK2 becomes the major enzyme to produce phosphoenolpyruvate, and therefore FBP2 is the key enzyme for the production of fructose-6-phosphate in brain metastatic cells. To test the role of FBP2 in the glucose independence of MDA-MB-231Br3 cells, the survival rate of MDA-MB-231Br3 cells can be measured when FBP2 is knocked down by shRNA. For example, FIG. 4B shows immunohistochemical staining of metastatic breast cancer in the brain for FBP2. Human breast cancer brain metastases are positive for FBP2 (arrows, bar=100 micrometers). In FIG. 4C, FBP2 is knocked down by shRNA in MDA-MB-231Br3 cells. As shown in FIG. 4D, knocking down of FBP2 results in a significant amount of MDA-MB-231Br3 cell death when those cells are cultured in a glucose-free medium. These results indicate that brain metastatic MDA-MB-231Br3 cells gain gluconeogenic capacity by up-regulating FBP2. To test whether FBP2 is also expressed in cancer cells of human breast cancer brain metastasis tissues, immunohistochemical staining of FBP2 can be performed on four samples of human breast cancer brain metastasis. By way of non-limiting example, FIG. 4E shows that FBP2 is expressed in cancer cells of breast cancer brain metastases. For these tests, trypanblue uptake can used to identify dead cells, and triplicates of samples can be used in each group.

Figure 5:
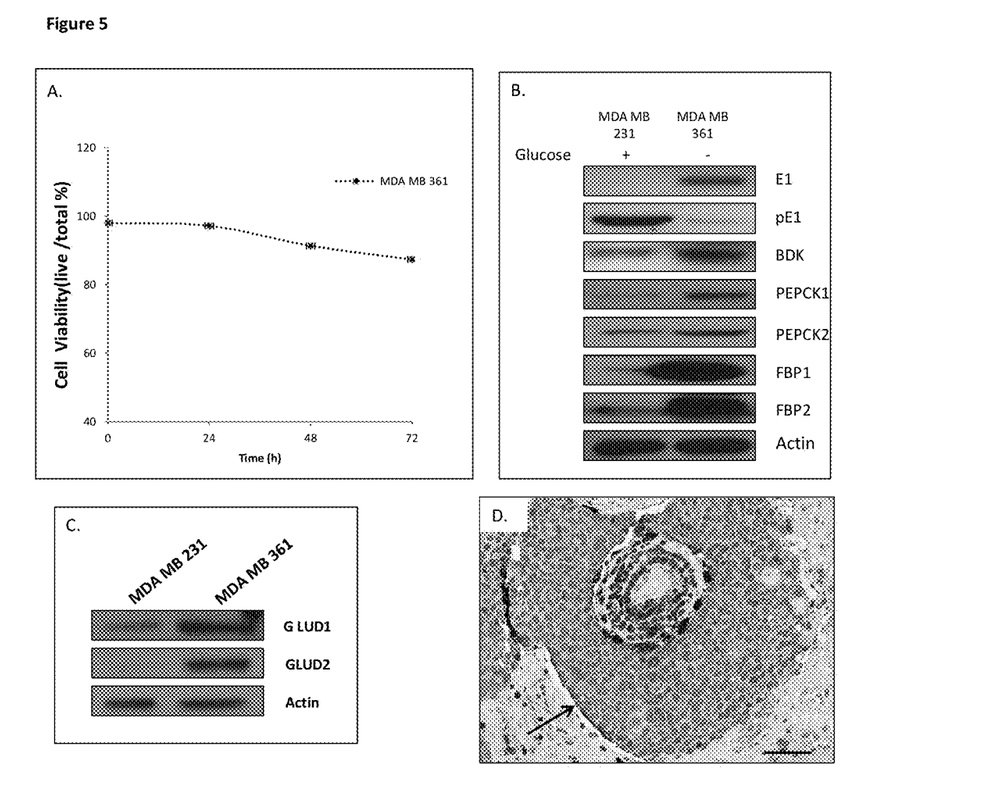
FIG. 5. Shows various characterizations of MDA-MB-361, a breast cancer brain metastatic line.

In other embodiments of the present invention metastatic cancer cells from MDA-MB-231Br3 cell line (derived mice brain tissues) exhibit similar glucose independent phenotypes to those obtained from a commercially available breast cancer metastatic cell line derived from human brain tissues (MDA-MB-361). Results show that both MDA-MB-231Br3 cells and MDA-MB-361 cells are completely viable in a glucose-free medium for 72 hours without refreshment of medium, as shown in FIG. 5A (triplicate samples used at each time point). MDA-MB-361 cells exhibit higher levels of total BCKDH-E1, but lower levels of pSer293-BCDKH-E1 relative to MDA-MB-231 cells. However the level of BDK is higher in MDA-MB-361 cells than in MDA-MB-231 parental cells, as shown in FIG. 5B. MDA-MB-361 cells contain even higher amount of enzymes for BCAA oxidation (E1 and pE1), gluconeogensis (PEPCK1, PEPCK2, FBP1 and FBP2), and GLUD1 and GLUD2. This data indicates an even stronger gluconeogenic capacity than that observed in MDA-MB-231Br3 cells, as shown in FIG. 5B. Expectedly, MDA-MB-361 cells are able to produce $^{13}$C-ribose-phosphate from $^{13}$C-glutamine (Table 2).

TABLE 2

$^{13}$C-glutamine produce$^{13}$C-phosphoribose can be detected in MDA MB 361 but not MDA MB 231

| Sample | ribose-phosphate | ribose-phosphate_$^{13}$C |
| --- | --- | --- |
| MDA MB 231 | 70914.7 +/− 28162.52 | ND |
| MDA MB 361 | 638787.2 +/− 312563.2 | 127854.2 +/− 20193.78 |

Table 2 $^{13}$C-glutamine produced $^{13}$C-phosphoribose can be detected in MDA MB 361 but not in MDA MB 231.

Similar to MDA-MB-231 cells, cancer cells of human breast cancer brain metastasis are also positive for FBP1, as illustrated in FIG. 5C. This data suggests that brain metastatic breast cancer cells derived from mice brain tissue and human brain tissue adopt similar and even stronger metabolic alterations. In addition, both cell types gain animo acids dependent gluconeogenenic capacity, and both possess an enhanced metabolism allowing them to consume BCAAs. Finally, as shown in FIG. 5D, human breast cancer brain metastases are positive for FBP1 (arrows, bar=50 micrometers).

Mutual adaptations between metastatic cancer cells and the microenvironment of a host organ have to be achieved for cancer metastasis to thrive. Alterations at levels of gene expression and activities of signaling pathways in cells of both cancer metastasis and host organs have been well documented (Kovacevic, Z. et al., Mitochondrial metabolism of glutamine and glutamate and its physiological significance. *Physiol. Rev.* 63, 547-605 (1983); Li, C., et al., Green tea polyphenols modulate insulin secretion by inhibiting glutamate dehydrogenase. *J. Biol. Chem.* 281, 10214-10221 (2006)). Cancer brain metastasis is known to be resistant to therapies (Chaffer, C. L. et al. A perspective on cancer cell metastasis. *Science* 331, 1559-1564 (2011)). In the present invention, breast cancer brain metastatic cells are able to (1) produce aerobic glycolysis, and (2) utilize oxidations of glutamine and branched chain amino acids, as well as part of the gluconeogenic pathway for producing glucose in a glucoeneogenic medium.

The brain interstitial space is a unique metabolic microenvironment. Because of the pre-metabolizing functions of astroglial cells that bridge blood vessels with neurons, the interstitial compartment of the brain is characterized with low levels of glucose (Fellows, L. K., et al., Extracellular brain glucose levels reflect local neuronal activity: a microdialysis study in awake, freely moving rats. *J. Neurochem.* 59, 2141-2147 (1992); Hu, Y. et al., Rapid changes in local extracellular rat brain glucose observed with an in vivo glucose sensor. *J. Neurochem.* 68, 1745-1752 (1997)), high levels of glutamate (Yudkoff, M., et al. Brain glutamate metabolism: neuronal-astroglial relationships, *Dev. Neurosci.* 15, 343-350 (1993)), and branched chain alpha-ketoacids (the first intermediate metabolite of BCAA oxidation) (Daikhin, Y. et al., Compartmentation of brain glutamate metabolism in neurons and glia. *J. Nutr.* 130, 1026S-1031S (2000)). Passing through the blood-brain-barrier, glucose is mainly taken up by astroglial cells and pre-processed in the astroglia for neuronal energy need (Pellerin, L., Brain energetics (thought needs food), *Curr. Opin. Clin. Nutr. Metab. Care* 11, 701-705 (2008)), which results in a 10 times lower interstitial glucose level as compared to the glucose level in the blood (Fellows, L. K., et al., Extracellular brain glucose levels reflect local neuronal activity: a microdialysis study in awake, freely moving rats, *J. Neurochem.* 59, 2141-2147 (1992); Hu, Y. et al., Rapid changes in local extracellular rat brain glucose observed with an in vivo glucose sensor. *J. Neurochem.* 68, 1745-1752 (1997)). The elevated expression of mRNA of genes involved in glycolysis in brain metastatic cells (Chen, E. I., et al. Adaptation of energy metabolism in breast cancer brain metastases. *Cancer Res* 67, 1472-1486 (2007)) might be a compensatory response to the low levels of glucose in the interstitial space of the brain. The high rate of glutamate synthesis in the brain requires an amino group donor that is readily transaminated. At least two thirds of the amino groups of brain glutamate are derived from BCAAs (Yudkoff, M., et al. Brain glutamate metabolism: neuronal-astroglial relationships, *Dev. Neurosci.* 15, 343-350 (1993)). The constant large scale uptake of BCAAs by the brain is sustained by large neutral amino acids transporters, which are highly expressed in the endothelial cells of brain vessels (Del Amo, E. M., et al., Pharmacokinetic role of L-type amino acid transporters LAT1 and LAT2, *Eur. J. Pharm. Sci.* 35, 161-174 (2008)). Astroglial cells produce glutamine for neurons via transfer of an amino group from BCAA to glutamate, and the byproducts of the transamination, branched chain α-ketoacids, are released to the interstitial space, where they can be taken up by neurons to use for metabolizing glutamine by deamination (Yudkoff, M., et al. Brain glutamate metabolism: neuronal-astroglial relationships, *Dev. Neurosci.* 15, 343-350 (1993)). The contribution of BCAAs to the survival of cancer brain metastasis is further supported by higher sensitivity of using $^{11}$C-BCAA as a tracer of imaging for brain metastasis than using glucose analogue tracer $^{18}$FDG (Ishiwata, K., et al. Re-evaluation of amino acid PET studies: can the protein synthesis rates in brain and tumor tissues be measured in vivo?, *J. Nucl. Med.* 34, 1936-1943 (1993); Ishiwata, K., et al., Brain tumor accumulation and plasma pharmacokinetic parameters of 2'-deoxy-5-18F-fluorouridine, *Ann. Nucl. Med.* 7, 199-205 (1993); Kirikae, M., et. al, Quantitative measurements of regional glucose utilization and rate of valine incorporation into proteins by double-tracer autoradiography in the rat brain tumor model, *J. Cereb. Blood Flow Metab.* 9, 87-95 (1989)), suggesting that brain metastatic cells uptake a high amount of BCAAs. The shift from glucose metabolism to amino acids metabolism for survival presented by brain metastatic cells, as described herein, further supports that the organ microenvironment plays a critical role in the development of cancer metastasis.

The sensitivity of brain metastatic cells to α-KG depletion indicates that a constant active TCA cycle is crucial for the survival of such cells, which is required to perform gluconeogenesis using amino acids as substrates. Gluconeogenic activity is not normally presented in cells that are not originated from liver, kidney, intestine or muscle (Previs, S. F., et al., Is there glucose production outside of the liver and kidney?, *Annu. Rev. Nutr.* 29, 43-57 (2009). The capacity to produce ribose from amino acids using part of the gluconeogenic pathway (by upregulation of FBP2) and to increase oxidation of amino acids provides the brain metastatic cells with the following: external glucose independent survival and proliferation skills, production of ATP from amino acids oxidation, and generation of building blocks for proliferation using the gluconeogenic pathway. Based on the expression of FBP2 and FBP1 in the human breast cancer brain metastases together with the data of brain metastatic cell lines, there is great potential for targeting amino acid dependent gluconeogenesis for the treatment of breast cancer brain metastasis.

Inhibitors of FBPs are well known and have been developed in laboratories with the goal of treatment of diseases such as diabetes (Kitas, E. et al., Sulfonylureido thiazoles as fructose-1,6-bisphosphatase inhibitors for the treatment of Type-2 diabetes, *Bioorganic & Medicinal Chemistry Letters* 20, 594-599 (2010); U.S. Pat. Nos. 7,371,739; 7,312,219; 7,285,543; 6,967,193; 6,919,322; 6,489,476; 6,399,782; 6,294,672; 6,110,903; 6,107,274; 6,054,587). These inhibitors include but are not limited to benzimidazole derivatives, aminopyridines, indole and azaindole inhibitors, sulfonylureido thiazoles, tricylic thiazoles, achyrofuran, (+)-Usnic acid, and 5'-adenosinemonophosphate mimics. Our current finding reveals that such inhibitors of FBPs could be used for prevention and treatment of cancer, including cancer brain metastases, by inhibiting FBPs or their respective pathways in a cancer patient. Therefore the present invention is useful in clinical applications. For example, an embodiment of this invention includes the discovery that FBPs play a role in the survival of cancer cells, and that a new use of known inhibitors of FBPs or their pathways is to treat cancer by administering a therapeutic composition comprising one or more inhibitors of FBPs to a cancer patient. Further embodiments include compositions that are adapted for use in conjunction with inhibitors of FBPs to treat cancer, including cancer brain metastases. The present invention is useful for the treatment of cancer patients, and other clinical applications.

While the invention described herein specifically focuses on compositions and methods for diagnosing and treating cancer cells using the fructose-1,6-biphosphatases (EC: 3.1.3.11) (FBPs, type 1 and type 2) and/or their respective pathway as targets, one of ordinary skills in the art, with the benefit of this disclosure, would recognize the extension of such approach to other systems.

While the invention described herein specifically focuses on novel compositions and methods of treating cancer by targeting FBPs or their pathways, one of ordinary skills in the art, with the benefit of this disclosure, would recognize the extension of such approaches to other systems. It will be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

EXAMPLES

Example 1

Establishment of a Brain Metastatic Breast Cancer Cell Line

MDA-MB-231 cell line was purchased from American Type of Cell Culture (ATCC). MDA-MB-231BR3 cell line was established by three rounds of in vivo cloning. Briefly, MDA-MB-231 cells were cultured in complete Eagle minimum essential medium (MEM) supplemented with 10% fetal bovine serum. Cells in exponential growth phase were harvested with 0.25% trypsin-0.02% EDTA solution (w/v). The cells were washed and resuspended in $Ca^{2+}/Mg^{2+}$ free Hanks' balanced salt solution (HBSS) before injected (1.0× $10^6$ cells/100 μl/injection) into the brain of female nude mice via the intracarotid artery according to previously published protocol (Yano, S., et al., Expression of vascular endothelial growth factor is necessary but not sufficient for production and growth of brain metastasis, *Cancer Res.* 60, 4959-4967 (2000)). Tumor bearing brain tissues were harvested at the 4th week after injections of tumor cells and tumor regions were dissected and digested in a solution containing collagenase (200 U/mL) and DNase (1500 U/mL) for 30 min at room temperature. Tumor cell suspensions were obtained by filtering the supernatants through a wire sieve. The cell suspensions were then cultured in fresh medium and the unattached cells were washed off at 48 hours after culturing. Tumor cells propagated by culturing in the same type of medium as used for culturing the parental MDA-MB-231 cells were injected into the brains of female nude mice for another round of in vivo cloning. This cloning procedure was repeated three times, which gave rise the MDA-MB-231Br3 cells. Injection of tumor cells into the mammary gland fat pad was done by first putting MDA-MB-231Br3 cells in complete Eagle minimum essential medium (MEM) supplemented with 10% fetal bovine serum. Cells in exponential growth phase were harvested with 0.25% trypsin-0.02% EDTA solution (w/v). The cells were washed and resuspended in $Ca^{2+}/Mg^{2+}$ free Hanks' balanced salt solution (HBSS) before injected (5,000 cells/100 μl/injection) into the fat pad of mammary glands of female nude mice (n=5). At the 12th week after tumor cell injection, the brains of tumor bearing mice were harvested for exhausting sequential sectioning to identify micrometastasis.

Example 2

Cell Survival Assay

Cells were seeded in 6-well plates in full MEM medium containing 5% dialyzed FBS and supplemented with 100 IU/ml penicillin and 100 μg/ml streptomycin (Invitrogen, CA, USA) and 292 ug/ml L-Glutamine (Invitrogen, CA, USA). Medium were replaced with modified MEM after 12 hours. Modified MEM contains basic formula of 5% dialyzed FBS and 100 IU/ml penicillin and 100 μg/ml streptomycin, other supplements like glutamine, glucose, etc.

were added in the basic formula according to different needs of experimental groups. Both cell culture medium and trysinized cells were collected after 48 hours and stained with trypan blue. Viability counting was counted by Countess® Automated Cell Counter (Invitrogen, CA, USA).

Example 3

Metabolic Assays

Glycolytic activity of cancer cells was determined by measuring glucose consumption and lactate production. Cells were seeded in 6-well cell culture microplates at $0.5\text{-}1\times10^6$ cells/well/3 ml according to their growth rate and allowed to attach overnight. Fresh medium was replaced the next morning approximately 3 hours prior to the assay. Cell culture medium was sampled at 200 μl at three time points at 3 hours intervals. The glucose and lactic acid concentrations of the cell culture medium were measured using a Dual-Channel Biochemistry Analyzer-2700D (YSI Life Sciences). For each time point, triplicate samples were measured to calculate the average values. Cell numbers were counted with a Beckman Coulter analyzer to normalize the glucose and lactic acid concentrations. The levels of amino acids, glutatmine, glutamate, valine, leucine and isoleucine were measured by HPLC at the co-facility of Medical Genetics Laboratories of Baylor College of Medicine, Houston, Tex.

Example 4

Determination of the Activity of BCAA Oxidation $^{14}$C-leucine was added into the cell culture medium at a concentration of 2.0 μM. To absorb $CO_2$, a filter paper pad of 2.5 cm diameter soaked with 1 ml hydroxide of haymine was inserted into the ventilation cap of the T-75 cell culture flask. After 8 hours of culturing, the filter paper pads were removed and inserted into scintillation counter vials containing 4 ml scintillation liquid. The radioactivity of $^{14}$C was measured by a Liquid Scintillation Analyzer, Tri-Carb 2810TR (PerkinElmer). Triplicates of sample of each experimental group were measured.

Example 5

Measurement of Metabolites Levels Resulting from Ribose-Phosphate Metabolization Under Glucose-Free Culture Conditions Cells were cultured in glucose free medium containing 2.0 μM $^{13}$C-glutamine for 6 hours. The following protocol was used to extract metabolites. All samples were harvested at a non-confluent density ($1.5\text{-}2.0\times10^6$ cells). Metabolism was quenched and metabolites extracted by aspiration of media and immediate addition of 3.6 mL 80:20 methanol: water at −80° C., and transfer to a dry-ice bed to simultaneously lyse cells and quench metabolism. Cell remnants were scraped from the tissue culture dish and transferred, along with the methanol:water, into a 15 mL conical centrifuge tube. The resulting mixture was centrifuged at 14,000×g for 20 min, and the supernatant was moved to a new tube. A 1 mL portion of the supernatant was then dried under nitrogen gas, dissolved in 100 μL of aq. LC buffer, spun at 13,000×g for 10 min to remove any remaining debris. Metabolite levels of $^{13}$C-ribose-phosphate in samples were determined by negative mode electrospray LC-MS. Extracts were resolved by reverse-phase HPLC system and metabolites detected by triple-quadrupole mass spectrometry, using multiple-reaction monitoring.

What is claimed is:

1. A method of treating brain metastatic cancer, comprising:
    identifying a subject having brain metastatic cancer cells that depend on gluconeogenic capacity for growth and survival by up-regulating fructose-1,6-bisphosphatase (FBP); and
    administering to the subject a therapeutic composition comprising one or more inhibitors of FBPs or brain FBPs pathways;
    wherein administration of the one or more inhibitors reduces proliferation of the brain metastatic cancer cells by inhibiting FBPs that regulate gluconeogenesis pathways of the brain metastatic cancer cells.

2. The method of claim 1, wherein the brain cancer metastasis cells consist of breast cancer cells that have metastasized in the brain.

3. The method of claim 1, wherein the cancer cells survive in glucose-independent conditions.

4. The method of claim 1, wherein the cancer cells produce glucose via FBPs mediated pathways.

5. The method of claim 3, wherein survival of the brain metastatic cancer cells depends on an active tricarboxylic acid cycle sustained by α-KG derived from glutamine or glutamate oxidation.

6. The method of claim 3, wherein the brain metastatic cancer cells are capable of consuming valine, leucine, and isoleucine (BCAAs).

7. The method of claim 1, wherein the one or more inhibitors of FBPs or FBPs pathways are one or more of 5'-adenosinemonophosphate mimics, benzimidazole derivatives, aminopyridines, indole and azaindole inhibitors, sulfonylureido thiazoles, tricyclic thiazoles, achyrofuran, or (+)-Usnic acid.

8. A method of treating brain metastatic cancer, comprising:
    identifying a subject having brain metastatic cancer cells that depend on gluconeogenic capacity for growth and survival by up-regulating fructose-1,6-bisphosphatase (FBP); and
    administering to the subject a therapeutic composition comprising shRNA;
    wherein administration of the shRNA reduces proliferation of the brain metastatic cancer cells by down-regulating FBPs that regulate gluconeogenesis pathways of the brain metastatic cancer cells.

9. A method of treating brain metastatic cancer, comprising:
    identifying a subject having brain metastatic cancer cells, wherein the brain metastatic cancer cells consist of breast cancer cells that have metastasized in the brain; and
    administering to the subject a therapeutic composition comprising shRNA;
    wherein administration of the shRNA reduces proliferation of the brain metastatic cancer cells by down-regulating FBPs that regulate gluconeogenesis pathways of the brain metastatic cancer cells.

* * * * *